(12) United States Patent
Danielsson et al.

(10) Patent No.: US 9,460,822 B2
(45) Date of Patent: Oct. 4, 2016

(54) COLLIMATOR ARRANGEMENT AND METHOD

(75) Inventors: Mats Danielsson, Eindhoven (NL);
Torbjörn Hjärn, Eindhoven (NL);
Daniel Säll, Eindhoven (NL); Markus Wahlberg, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 284 days.

(21) Appl. No.: 13/993,161

(22) PCT Filed: Oct. 24, 2011

(86) PCT No.: PCT/EP2011/068501
§ 371 (c)(1),
(2), (4) Date: Oct. 3, 2013

(87) PCT Pub. No.: WO2012/079814
PCT Pub. Date: Jun. 21, 2012

(65) Prior Publication Data
US 2014/0016742 A1  Jan. 16, 2014

Related U.S. Application Data

(60) Provisional application No. 61/422,227, filed on Dec. 13, 2010.

(30) Foreign Application Priority Data

Dec. 13, 2010 (SE) ........................... 1051307

(51) Int. Cl.
*G21K 1/02* (2006.01)
*A61B 6/06* (2006.01)
*A61B 6/00* (2006.01)

(52) U.S. Cl.
CPC ............... *G21K 1/025* (2013.01); *A61B 6/06* (2013.01); *A61B 6/502* (2013.01)

(58) Field of Classification Search
CPC ........... A61B 6/06; A61B 6/10; G21K 1/02; G21K 1/025; G21K 1/04; G21K 1/046
USPC .......................................... 378/37, 147–151
See application file for complete search history.

(56) References Cited

U.S. PATENT DOCUMENTS 4,489,426 A * 12/1984 Grass et al. ................... 378/150
6,054,712 A    4/2000 Komardin et al.
(Continued)

FOREIGN PATENT DOCUMENTS

EP    0417964 A2    5/1990
WO    02065209 A1   8/2002

*Primary Examiner* — Jurie Yun

(57) ABSTRACT

The present invention relates to a method and an X-ray apparatus comprising an X-ray source, an x-ray detector, and at least a first collimator having a first active position and a second collimator having a second active position for forming a bundle of X-ray beams, wherein both of said active positions are located in a substantially straight path between said X-ray source and said detector, but at different distances from said X-ray source. The X-ray apparatus further comprises a selector arrangement for switching one of said first or second collimators in said first or second active position, whereby when one of said first or second collimators is in an active position the other collimator is in an inactive position.

28 Claims, 13 Drawing Sheets

(56) References Cited

U.S. PATENT DOCUMENTS

| | | |
|---|---|---|
| 6,483,891 B1 | 11/2002 | Lazarev et al. |
| 6,621,891 B2 | 9/2003 | Danielsson |
| 7,016,458 B2 | 3/2006 | Francke |
| 7,020,237 B2 | 3/2006 | Francke et al. |
| 7,302,031 B2 | 11/2007 | Hjarn et al. |
| 7,440,539 B2 | 10/2008 | Danielsson et al. |
| 7,664,223 B1 | 2/2010 | Danielsson et al. |
| 8,611,490 B2 | 12/2013 | Zhang |
| 2003/0012341 A1 | 1/2003 | Danielsson |

* cited by examiner

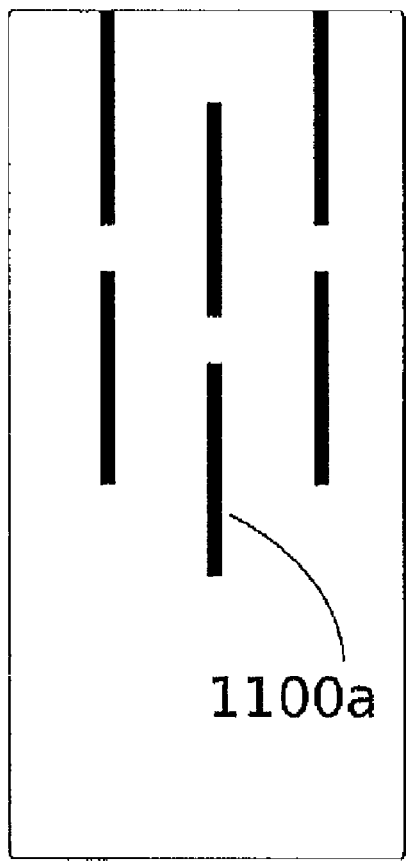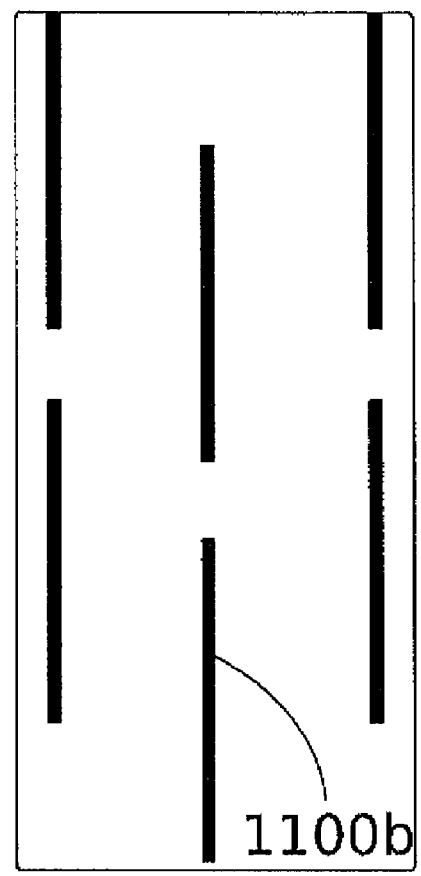
FIG. 11a
FIG. 11b

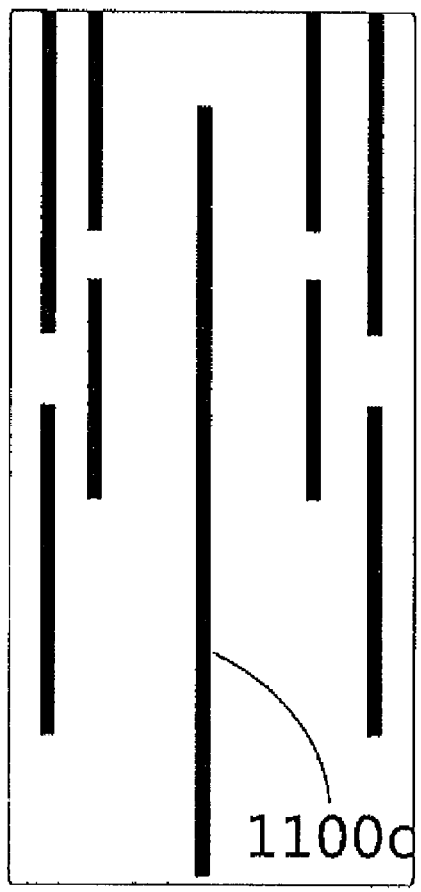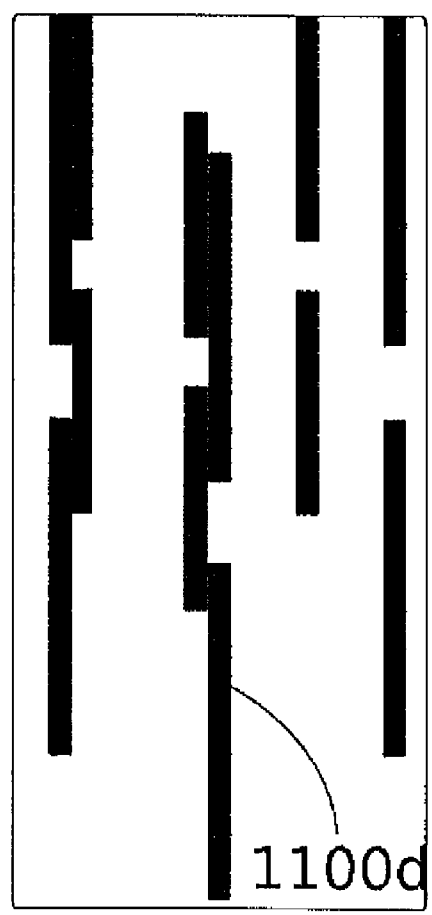
FIG. 11c
FIG. 11d

COLLIMATOR ARRANGEMENT AND METHOD

TECHNICAL FIELD

The present invention relates to a method and arrangement in an X-ray apparatus for scanning using a bundle of X-ray beams, and specially a collimator arrangement in an X-ray apparatus.

BACKGROUND

According to prior art, photon counting multi-slit scanning enables X-ray imaging, in particular mammography, with a low X-ray dose and effective rejection of scattered photons. Examples of multi-slit scanning apparatuses are presented in U.S. Pat. Nos. 7,302,031; 7,016,458 and 7,020,237 and also illustrated in FIGS. 1-2. In a typical multi-slit scanning X-ray apparatus, the X-rays are detected by a set of line detectors. A multi-slit collimator is located between the X-ray source and the imaged object. The multi-slit collimator forms a bundle of X-ray beams that matches the pattern of the line detectors. The bundle of X-ray scans through the imaged object, and an image is constructed by accumulation of data from the line detectors. In the apparatus of FIG. 1, for example, the scanning is performed by rotating a scan arm, which is basically a rigid shaft with an X-ray source (110), a multi-slit collimator (120) and a package of line detectors. For example, a human breast may be arranged between a compression paddle (140) and a support above the detector package. A position encoder measures the position of the compression paddle, which is equal to the breast thickness, which is used to optimize a voltage in the X-ray source.

The collimator itself may be a tungsten plate with narrow elongated apertures, referred to as slits. The tungsten plate lacks rigidity in transverse direction, and is therefore arranged in a frame, typically made of carbon fibers, which is reasonably susceptible to X-rays. Different examinations may benefit from different setup of multi-slit collimators, For example, thin collimator slits enable better image resolution than wide slits, but wide slits allow larger X-ray flux and thus shorter total time for image acquisition. U.S. Pat. No. 6,621,891, for example, presents a method and arrangement for controlling collimator slit widths, using two layers of collimators, moving relative to each other.

The collimator has been designed to work in a position which enables imaging of different object thicknesses, e.g. thick breasts as well as thin breasts. It can be easily understood that the collimator impacts image resolution. The X-ray source has a focal spot of a size that is not negligible, which causes blur. The combination of a big focal spot and a collimator far from the object may cause the thin X-ray beams to spread substantially before reaching a small imaged object. FIG. 3 presents an exaggerated illustration of blur due to a large focal spot size and a collimator being placed close the X-ray source. Usually, a collimator, according to prior art, works at only one distance from the X-ray source, due to different magnification factors of the cone beam geometry. Simply displacing the collimator closer to the X-ray source would widen the bundle of beams, and the beams would no longer hit the line detectors. It is possible to use a different collimator at different distance, provided that collimator is resized relative to the original. A collimator may be manually switched by a human operator. The switching is intended for switching between different applications, such as normal breast imaging and biopsy mode. The manual switching is however too slow for a typical screening mammography workflow. The collimator must be attached by a rigid mechanism at high repetitive accuracy. For patient safety, it must be verified or inspected that the collimator is properly attached. Above the multi-slit collimator, the X-ray flux is very high, and the patient would receive an unacceptable dose if X-rays pass outside the collimator slits.

The robustness of the collimator is critical for image resolution, which calls for carefulness in every design of the collimator and surrounding mechanics. The collimator position and slit width shall be invariant to rotation of the X-ray apparatus for acquiring mediolateral oblique view (MLO) images at 45-60 degrees, mediolateral view (ML) images at 90, and 180 degrees images for patients with disabilities. In addition, the space is very limited around the collimator. In mammography, there is virtually no space in front of the collimator, as the patient's breast is imaged very close to the patient's ribs. The space is also limited on the left and right, due to the need of acquiring ML/MLO images close to the patient's shoulder.

The collimator's position must also be possible to calibrate relative the X-ray source and the line detectors. At least, the collimator position must be adjustable essentially orthogonal to the slits, in both ends of the collimator, i.e. a small rotation and translation in a plane mainly transverse the direction of X-rays. In existing techniques, tolerance of adjustment is typically 30 micrometers transverse to the slit direction. In other directions, the tolerances are moderate, but still call for rigidity and calibration. According to prior art, each collimator's position may be calibrated relative a holder, which in turn is rigidly attached to the system.

The collimator may also be displaced between examinations, e.g. according to patent U.S. Pat. No. 7,664,223. According to the apparatus in FIGS. 1-2, the collimator is arranged to be displaced vertically along a scan arm, towards a rest position near the X-ray source. The scan arm is essentially a rigid shaft for carrying the X-ray tube, the collimator and the detector.

There may also be a radiation cover, e.g. according to U.S. Pat. No. 7,440,539, which must be attached in a way that the collimator does not deflect due to the weight of the cover.

SUMMARY

Thus, one object of the present invention is to improve image resolution in an X-ray apparatus, wherein the resolution depends on the collimator.

Calculations and simulations for an apparatus, e.g. according to FIGS. 1-2, reveal that reduction of collimator blur, as described in conjunction with FIG. 3, can substantially improve image resolution. Preferably, the X-ray apparatus may be an apparatus according to FIGS. 1-2 or similar, or a tomosynthesis apparatus, or any other multi-slit scanner.

The present invention may reduce the blur for objects of different size (thickness) such as small and normal breast sizes without compromising the ability to acquire images of thick objects (breasts). The present invention provides for automatic switching between collimator positions, depending on available space or breast thickness, preferably as a result from a measurement by a compression paddle. The pattern of collimator slits may also be switched to match the detector pattern at the different distances. Due to cone beam geometry, the different patterns are roughly magnifications of the same pattern, wherein the magnification is proportional to the distance from the X-ray source. In a more general case, in case of tilted or curved collimators, the patterns match with some cone beam projection, a.k.a. perspective projection, wherein the surface of the first pattern is projected to the surface of the second pattern.

One aspect of the present invention involves a method and arrangement, comprising at least two different multi-slit collimators for at least two different distances from the X-ray source. One collimator is inactive while the other is active. The present invention also involves a selector means for automatic switching between the collimators.

The present invention also addresses patient safety, and robustness to potential failure modes. The patient will not risk being exposed to a high dose, even in the presence of, e.g. a control failure, a sensor malfunction, a simple electrical failure, or a potential mechanical failure. X-rays are prohibited to reach the patient in larger doses than what passes through the slits of one collimator. According to the safety aspect of the present invention, one collimator cannot move away from the active position, without another collimator moving in. In case there is a glitch between the two collimators, it can be covered. A preferred cover is an X-ray opaque material, attached between the two collimators. In one embodiment a cover may move in during the glitch.

Another aspect of the present invention is integration of a mechanism for calibration of collimator position. The collimator position may be calibrated, at least in a direction transverse the slits. Preferably, the present invention involves calibration means which does not take extra space, adding extra weights or prolonging tolerance chains. The present invention addresses the need for individual calibration of each collimator. Preferably, a calibration device such as a screw can be provided for each contact point, which are activated and deactivated depending on which collimator is active. The activation of the contact point may be implemented using a camshaft.

One aspect of the present invention addresses the combination of small tolerances, robustness to gravitational forces and the limited space. The collimator selector mechanics uses a shaft or axis, and springs to press the shaft or axis towards contact points. The contact points are preferably spread apart in the space behind the collimator. This solution reduces the impact of radial play on position and in particular angle. Preferably, at least two contact points are unique for each of the collimators.

Preferably the alignment calibration can be tested by moving the collimator in a substantially vertical direction and analyze which line detectors are in shadow. Preferably, the present invention allows each collimator to move straight vertically a short distance from the designated position, without moving the collimator in lateral direction, or switching to another collimator. Preferably but not exclusively, 10 mm is enough, as it causes shadows in the left-most and right-most detector lines, when the collimator is centered in lateral direction, and equally many lines are shadowed to the right and to the left.

The present invention also addresses rigidity and deflection in collimators. According to one aspect of the present invention, the two collimators are arranged alongside in an angle. The preferred angle is about 90 degrees when using two collimators, and roughly 120 degrees for an arrangement with three collimators. In one embodiment, the collimators may be attached in a rigid frame and potential gaps may be covered by an X-ray opaque material.

Switching between collimators involves a rigid rotation, around an axis. At least radial play is handled by applying pressure by at least one spring in one direction and pressing the axis to contact points that are spread apart along the axis.

One aspect to resize the pattern of a collimator slits, by moving two or more collimator sheets relative each other. It is a feasible solution with a novel and inventive choice of patterns in each sheet, whereby different patterns are obtained by a miniature relative displacement. High accuracy is required for controlling the slit width, as its width shall not vary from time to time more than a fraction of a percent, independently of temperature or gravitational forces. Preferably, the detector geometry shall also be adapted to reduce complexity of the patterns in the sheets. One such detector adaption may be to place the line detectors in straight lines, at equal distance. Collimator plate rigidity also calls for complex manufacture when making long slits or slits being very close.

The present invention is not limited to handling variations of sizes of human body parts. Different examination types benefit from different collimator positions. For example, the biopsy mode can be obtained in a more convenient way than manually switching collimators by removal and replacement of mechanical parts. Some examination types, e.g. biopsy, also benefit from other variations of the collimator, such as slit width and limited image field.

According to one aspect of the invention, an X-ray apparatus is provided for obtaining an image of an object, the apparatus comprising an X-ray source, an X-ray detector, a set of two or more multi-slit collimators, a collimator selector means, wherein the detector is characterized by detector pattern of several X-ray sensitive areas, and each of the collimator having a designated position between the X-ray source and the detector, and each of the collimators comprising narrow apertures arranged to match the detector pattern whenever the collimator is positioned in its the designated position, and furthermore the selection means is characterized by ability for automatically switching between collimators in the set of collimators and corresponding active positions. The X-ray apparatus further comprises a boundary sensing means for measurement position related to available space, and the selection means being setup to depend on information from the boundary sensing means. The X-ray apparatus further comprises means for adjusting the position of one of the collimators relative to the position of another of the collimator, at least in a direction transverse to the direction of the narrow apertures. The X-ray apparatus further comprises means for individually adjusting each collimator's position, in a direction transverse to the direction of the narrow apertures. The X-ray apparatus further comprises a common carrying member for carrying the set of collimators, and a means for rotating the carrying member relative to the detector and the X-ray source. The X-ray apparatus further comprises a displacement means for moving the carrying member towards along a path towards and away from the object, and the angle of the carrying member is controlled by springs and mechanical contact along the path.

The invention also relates to an X-ray apparatus comprising a gauge to measure object thickness, an X-ray source, several narrow X-ray receivers arranged in a detector pattern, a scanning means, a switchable multi-collimator means for forming a bundle of X-ray beams, the multi-collimator means being arranged to switch between at least a first and second pattern of narrow apertures, wherein the first pattern matches the detector pattern at a first distance from the X-ray source and the second pattern matches the detector pattern at a second distance from the X-ray source, wherein the first distance is substantially different from the second distance. The X-ray apparatus further comprises a selector means for automatically selecting the first or the second pattern of apertures. The selector means may be arranged to depend on a value from the gauge.

The invention also relates to a method for generating an image of an object in an X-ray apparatus comprising an X-ray source and a several X-ray receivers, and several narrow apertures. The method comprises the steps of mechanically measuring a boundary position of the object, selecting a distance from the X-ray source, moving several narrow apertures to the distance and along the ray paths between the X-ray source and the X-ray receivers, wherein the selecting of distance is dependent upon the measured boundary position, generation of X-rays passing through the apertures to the line detectors. The invention also relates to an X-ray apparatus with a computer user interface or a controller for switching between collimators, either directly or indirectly with respect to a selection in the user interface, i.e. working mode or type of medical examination to perform.

The invention also relates to an X-ray apparatus for imaging of a human breast, a compression paddle, a position sensor for measuring a position of the compression paddle, an X-ray source, a set of line detectors and multi-collimator means, further comprising at least a first and a second set of narrow elongated X-ray susceptible apertures through one or several plates, wherein the relative positions of the first X-ray susceptible apertures are projections of the line detectors to the plate or plates at a first distance from the X-ray source, and the second X-ray susceptible apertures are projections of the line detectors to the plate or plates at a second distance from the X-ray source, and furthermore the X-ray apparatus comprising a means for selecting one of the set of apertures depending on a value from the position sensor, and furthermore the first distance is different from the second distance. The plates are arranged on a carrying member with possibility to rotate, at least between a first and a second angle. The X-ray apparatus may further comprise a means for covering either first set of apertures or the second set of apertures.

The invention also relates to a computer program comprising a set of instructions for receiving a position of a compression paddle, selecting a collimator position based on the position.

The invention also relates to a collimator device for use in an x-ray apparatus. The collimator device comprises: a first and a second collimator arranged relative in an angels other than zero, and an axis for rotating the collimator device.

The invention also relates to a collimator device for use in an x-ray apparatus. The collimator device comprises: a first and a second collimator arranged distanced relative each other and configured to be placed in a first or a second active position for forming bundles of X-ray beams.

The invention also relates to a switchable multi-slit collimator device for use in a scanning X-ray apparatus, comprising at least two plates of X-ray opaque material, and a selector means for moving the plates. The plates comprises X-ray susceptible apertures, and the ensemble of the plates together with the selector means being adapted to generate at least a first and a second pattern of a number of narrow slits. The first pattern essentially matches the second pattern at a cone beam projection.

BRIEF DESCRIPTION OF THE DRAWINGS

In the following, the invention will be further described in a non-limiting way under reference to the accompanying drawings in which:

FIGS. 11a and 11b illustrate exemplary slit patterns for different collimator heights, and 11c and 11d illustrate two collimator sheets for generating the patterns.

DETAILED DESCRIPTION

In the following description the same reference signs refer to same parts throughout the drawings.

For simplicity reasons, the present invention is described with reference to an apparatus as presented in FIGS. 1 and 2, and the apparatus is arranged in an angle such that the X-ray source is straight above the detector. The apparatus may be configured to be rotated. It should be noted that neither the invention nor its embodiments are limited to any particular angle.

Figure 1:
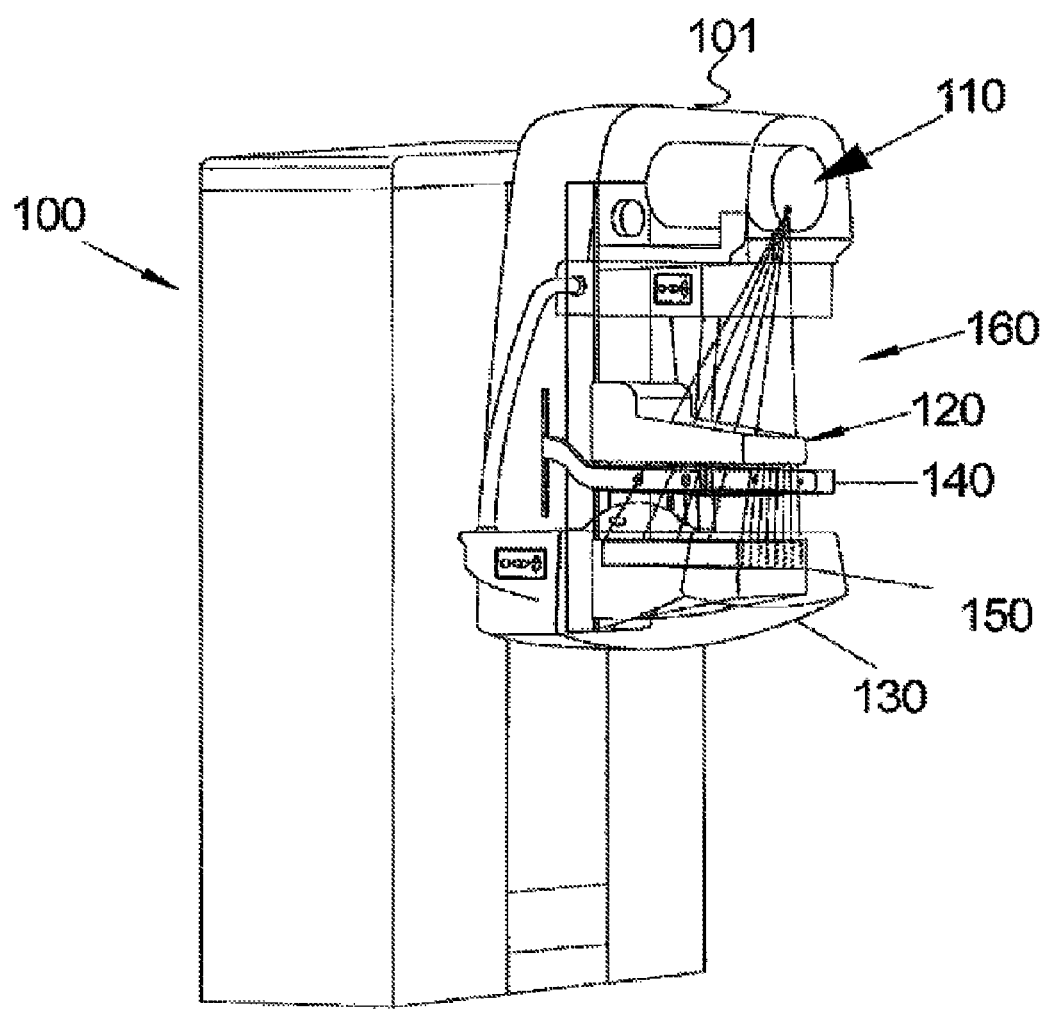
FIGS. 1 and 2 show a multi-slit scanning X-ray apparatus for mammography according to prior art.
Figure 2:
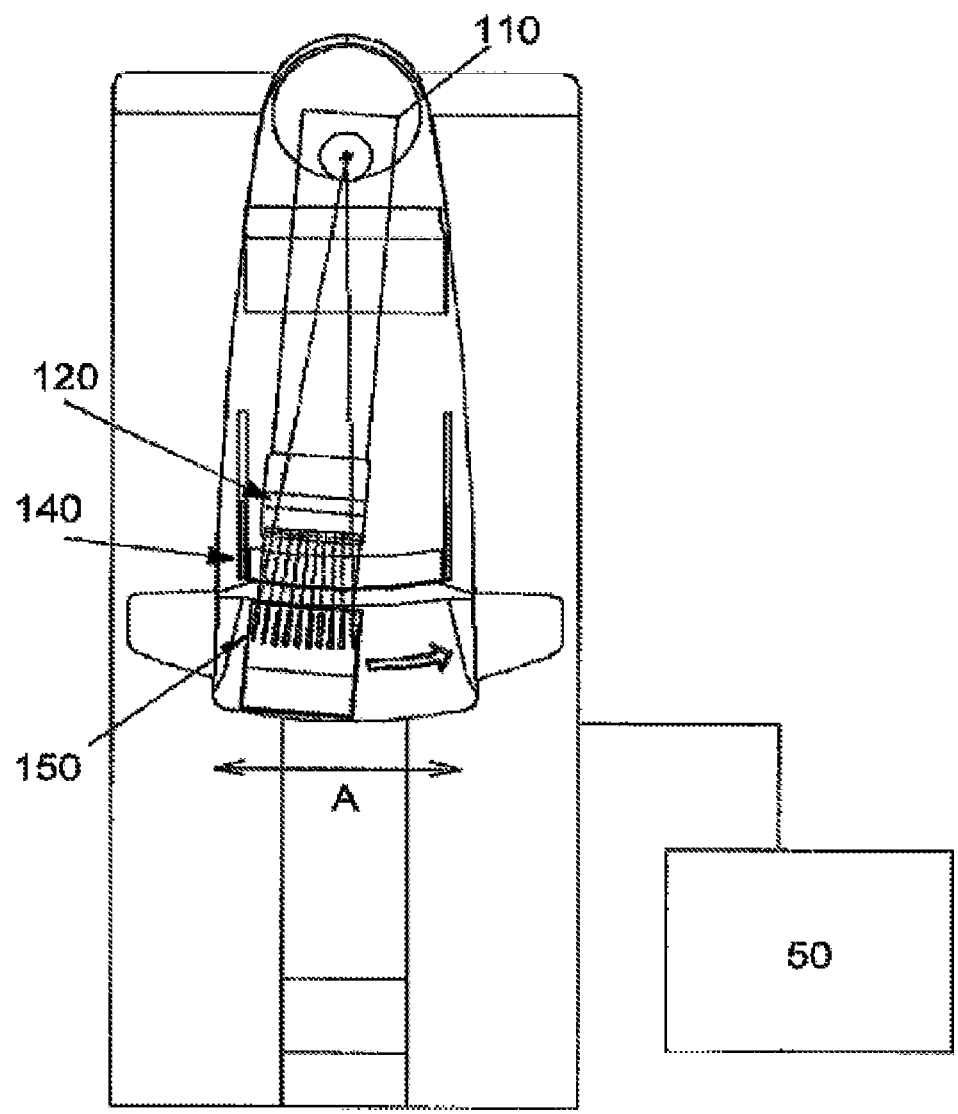
Figure 3:
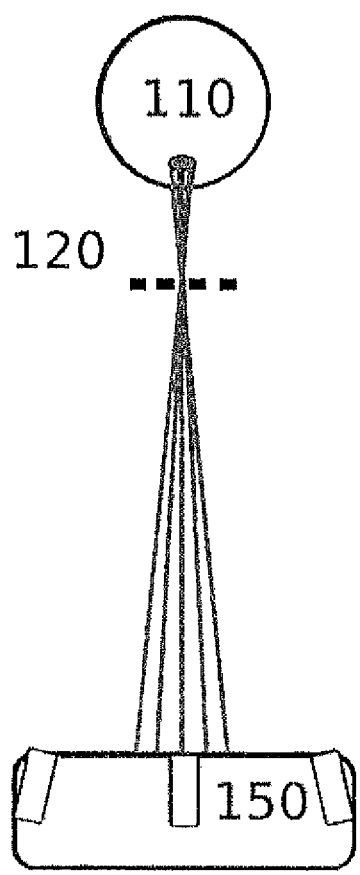
FIG. 3 is an exaggerated illustration of the drawback of placing the collimator close to an X-ray source with a big focal spot, resulting in blurred X-ray beam.

According to the present invention, an apparatus similar to FIGS. 1 and 2 selects a collimator height depending on available space, preferably measured by the compression paddle (140) or other measuring equipment, and selects a vertical position for the collimator and corresponding aperture pattern for that collimator position.

Figures 4A, 4B:
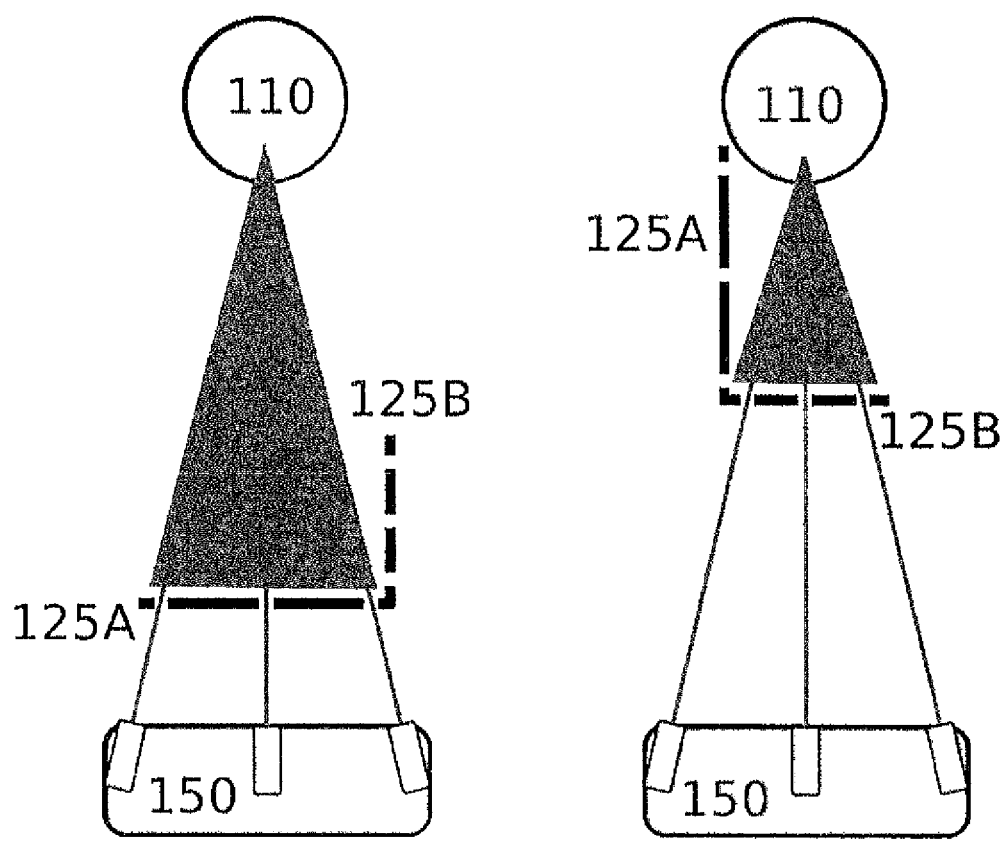
FIGS. 4a and 4b are a schematic views of a two multi-slit collimators fort two different distances from an X-ray source, arranged alongside in a 90 degree angle and switchable by a rotation of 90 degrees.

The preferred embodiments are implemented in a system, e.g. according to prior art illustrations of FIGS. 1 and 2, or similar. The apparatus (100) comprises an X-ray source (110), a package of line detectors 150, a compression paddle (140) support 130. For example, a human breast may be arranged between a compression paddle (140) and a support (130) above the detector package. The rays are designated with (160). The apparatus may communicate with a computer system (50). A position encoder (not shown) may be arranged to measure the position of the compression paddle, which is equal to the breast thickness, which is used to optimize a voltage in the X-ray source. The single collimator (120) is thus replaced by an assembly containing two collimators (125A) and (125B) (FIGS. 4a and 4b), according to this exemplary embodiment. Each collimator is designed to work at an individual distance from the X-ray source. For each collimator, reference is made to this position as an active position. The angle is also part of the active position. In the preferred embodiments, a collimator is active when inserted into the ray path between the X-ray source and the detector in an angle for blocking X-rays, except for the slits. However, active does not refer to vertical position. In some embodiments, the collimator can move (at least) a short distance in a vertical direction, without being deactivated. One embodiment takes advantage of the means for vertical collimator movement.

Figure 5:
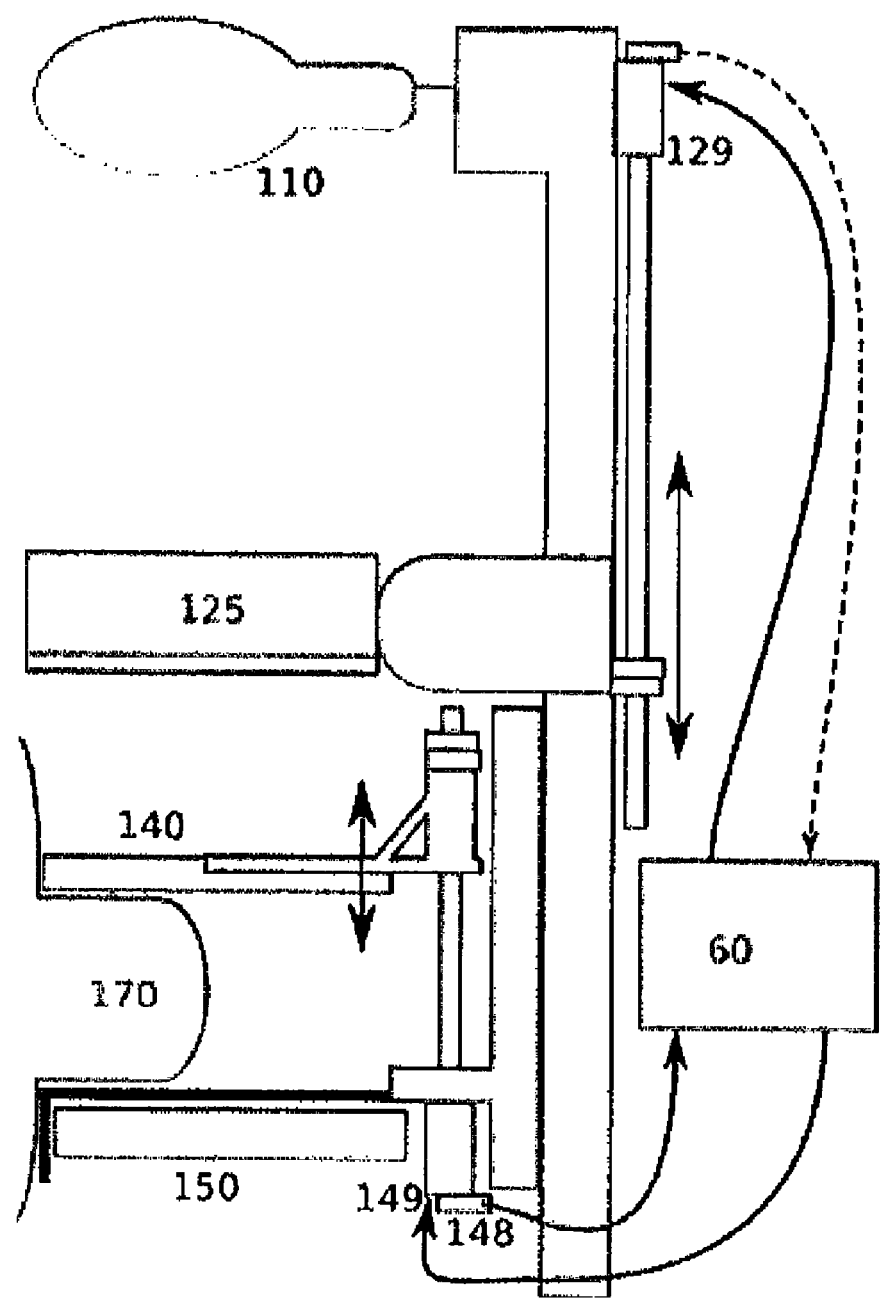
FIG. 5 illustrates a side view of selection of collimator height depending measured breast thickness.

In FIGS. 1 and 2, and FIG. 5, the compression paddle (140) is controlled by a motor (149), and position encoder (148) is attached to the motor shaft. In the preferred embodiment, a controller (60) receives the value from the position encoder and determines both a voltage in the X-ray source (110) and the position of the collimator and/or which collimator to use. In normal operation, the apparatus chooses the available collimator position closest to the breast or paddle, and a selector mechanism activates the corresponding collimator. Determination of the collimator to be activated is typically result of breast thickness, or more specifically the position of a compression paddle. The controller controls a motor (129) for moving the collimator in vertical direction to its designated height. In the preferred embodiment, the determination of collimator is implemented in a chain of dependencies, wherein the collimator selection depends on the voltage of the X-ray source voltage, which in turn depends on the combination of compression paddle position and selected dose level, and the collimator position depends on the voltage. A slight variation is a look-up-table, wherein the collimator selection depends on the measured breast thickness and the selected dose level.

The selector mechanism activates one collimator, and de-activates the other. The present invention involves different embodiments of selector mechanisms. In one embodiment, the selector mechanism takes advantage of the existing vertical motion rather than adding any additional motor or actuator.

Figure 6:
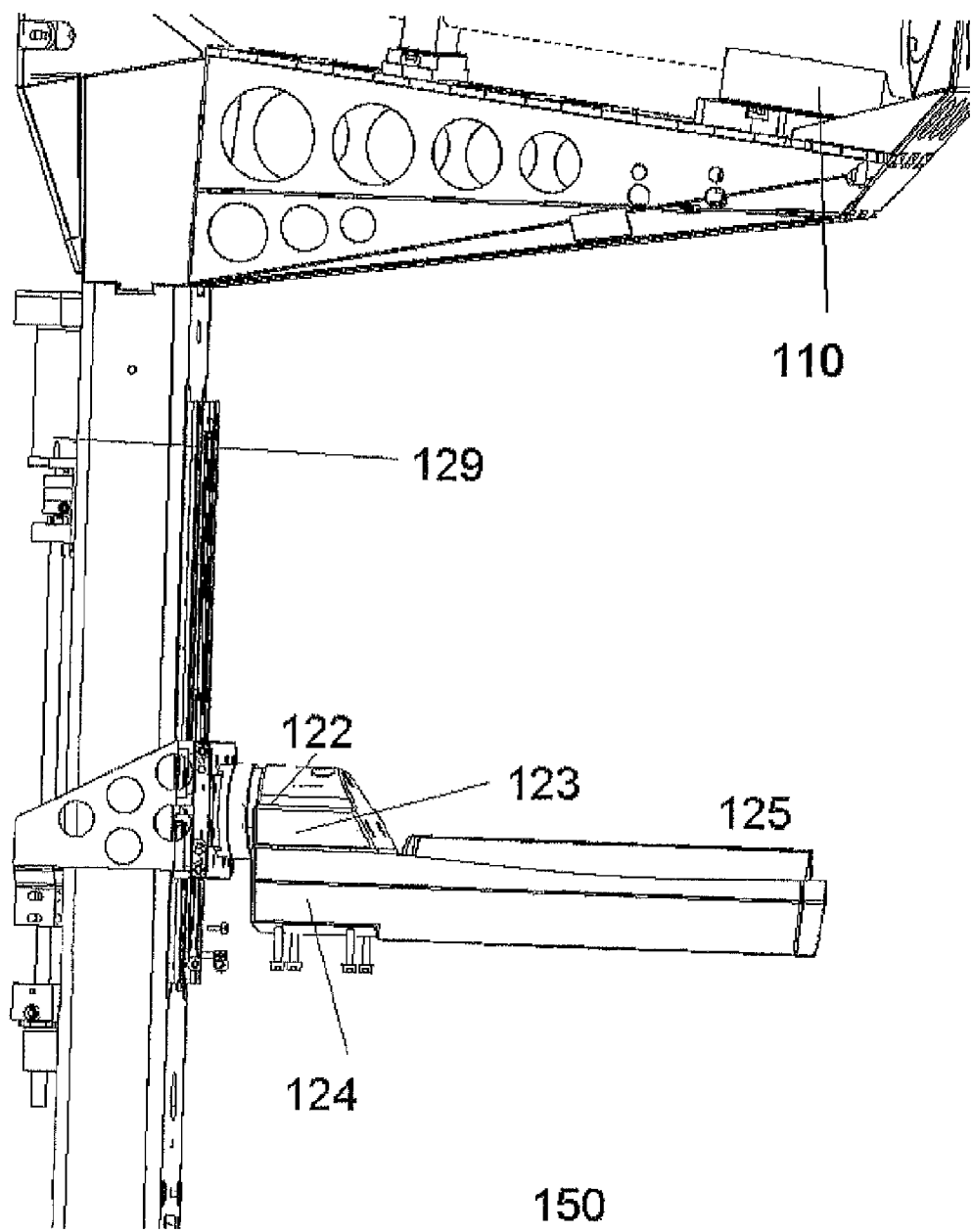
FIG. 6 shows an overview of a dual collimator and selector mechanics, partly covered by its carrying members and covers, according to one embodiment, mounted on a scan arm with motor for vertical collimator displacement.
Figure 7:
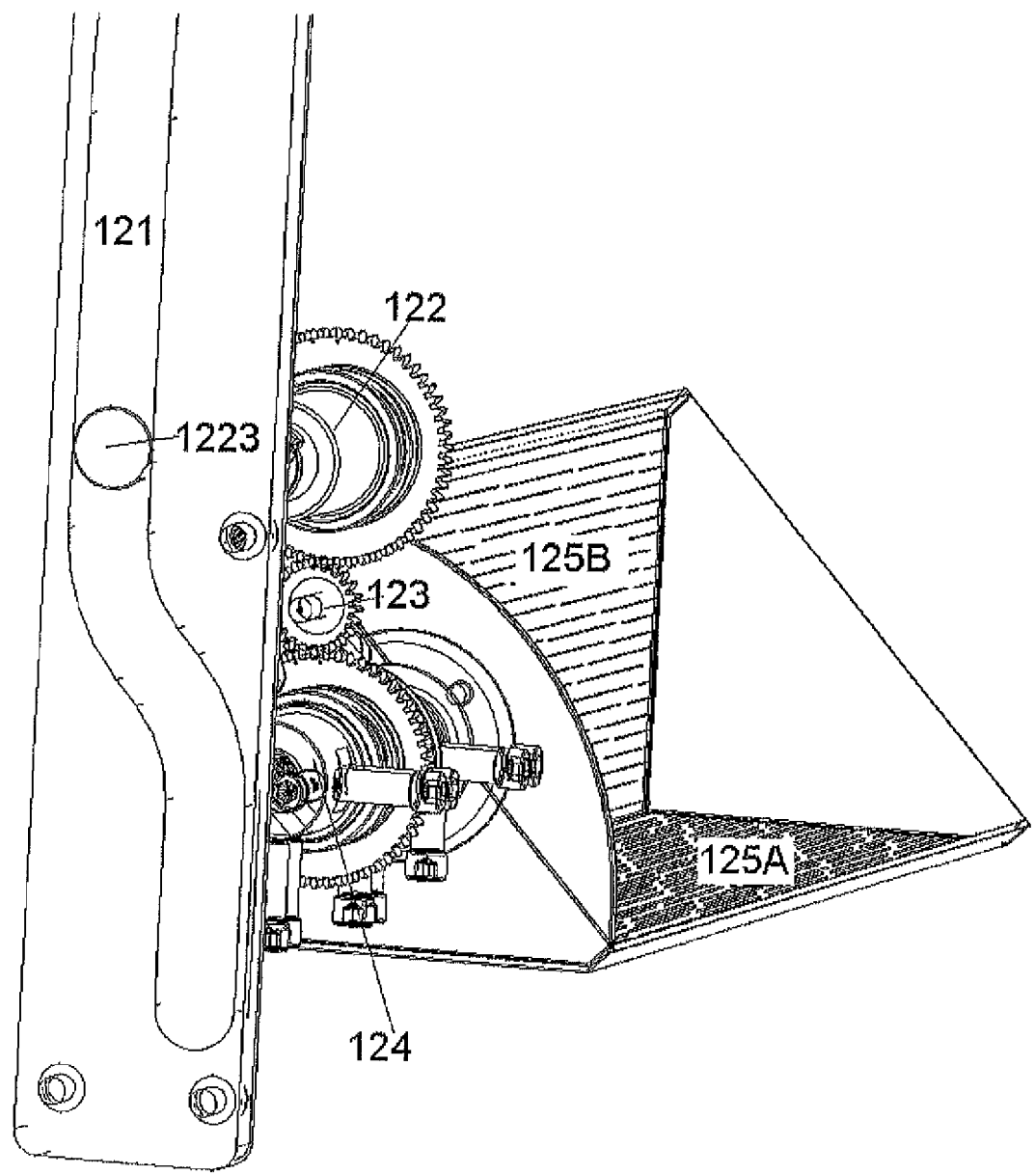
FIG. 7 is a view from behind, illustrating a dual collimator and its selector mechanics for one embodiment of the invention.
Figure 8:
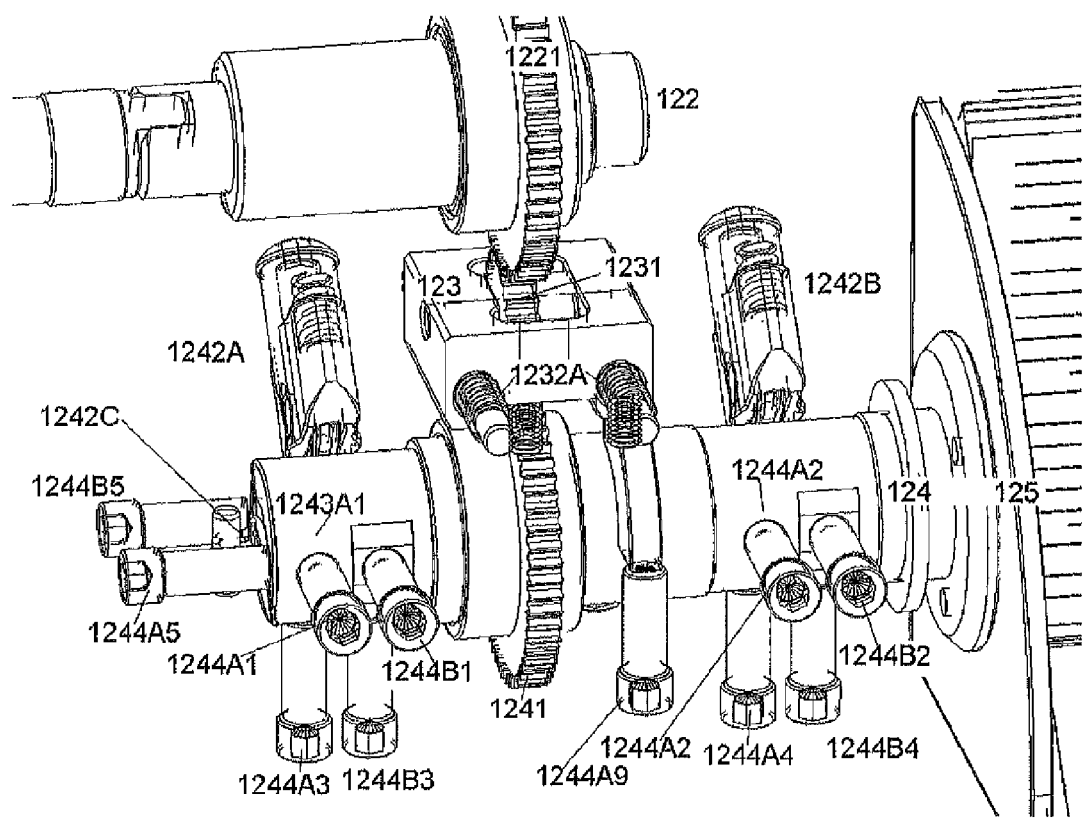
FIG. 8 illustrates the camshaft, and critical parts of the mechanisms for controlling the camshaft.
Figure 9:
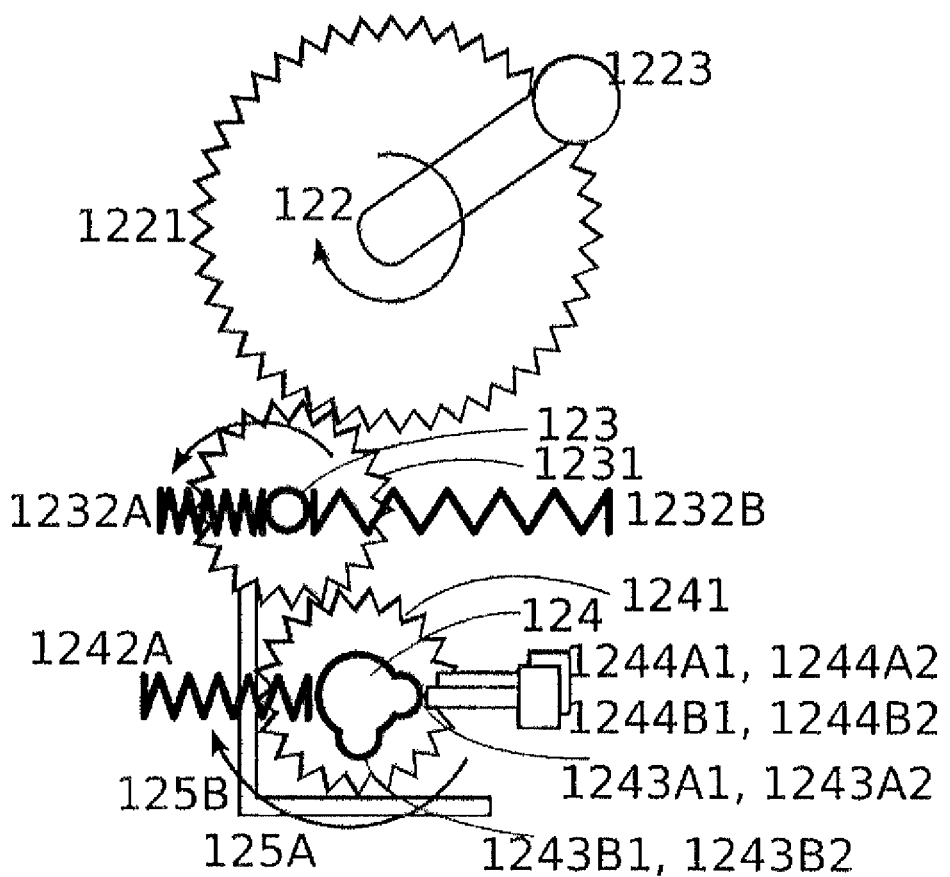
FIG. 9 illustrates the selector mechanics, according to one embodiment invention, viewed from the scan arm.
Figure 10:
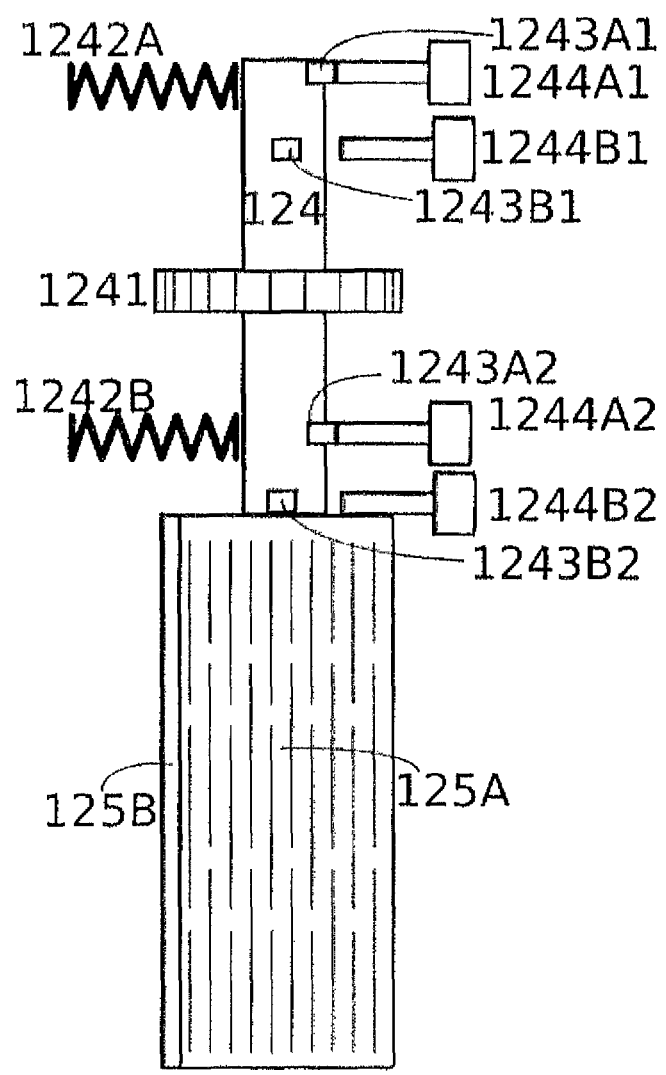
FIG. 10 illustrates, from below, the camshaft of FIG. 8 and adjustment screws according to one embodiment, viewed from below.

Embodiments of the selector mechanism are presented in FIGS. 6 to 10. FIG. 6 shows a dual collimator in a context including covers and the motor (149) for vertical collimator movements. FIG. 7 is a view from behind without covers. FIG. 8 is an illustration of the camshaft, and the mechanics for controlling its position. FIGS. 9 and 10 are simplified illustrations of the basic principle, viewed from the scan arm and below. These figures illustrate the three axes (122, 123, 124) with cog wheels (1221, 1231, 1241), springs (1232A-B, 1242A-B(-C)), camshaft (124) with a two sets of cams (1243A# 1243B#) and the corresponding sets of adjustment screws (1244A and 1244B), wherein # denotes a number 1-2 or 1-5 depending on different versions of the embodiment, FIG. 8 also presents screws (1244A9 and 1244B9) for limiting the angular interval of rotation of the camshaft (124). The camshaft is attached to a carbon fiber frame (125) which carries and two collimators (125A and 125B) arranged alongside in a 90 degree angle. FIGS. 7 and 9 also show the upper cog and its lever (1223) for touching a curved slide (121), which is mounted along the scan arm.

As shown in FIGS. 7-9, two multi-slit collimators are arranged side by side, in a 90 degree angle, in a frame of carbon fiber (125). The gap between the two collimators is negligible or covered by a piece of X-ray blocking material (not shown), e.g. a metal tape, or a metal cover outside the frame. The carbon fiber frame is rigidly attached to a camshaft (124). Parts (124) and (125) are together referred to as rotor, as they can rotate 90 degrees. There are mechanical limits for preventing rotation beyond the angles corresponding to the angles of each collimator being active.

The camshaft is designed to have a substantial radial play and also an axial play, whereby its position is controlled by its cams and springs for pushing the camshaft to tight contact in the active cams.

The preferred embodiment may comprise a number of adjustment screws (1244A-D), e.g. 5, for each collimator, thus a total of, e.g. 10 adjustment screws for two collimators. The camshaft comprises cams to contact the screws at the intended angle for the corresponding collimator, and released for the angles of the other collimator. Different sets of adjustment screws are active in different angles of the camshaft, thus allowing individual calibration for each of the two collimators. Each screw offers one degree of freedom. In another embodiment may only two adjustment screws per collimator be provided, but this requires slightly better mechanical manufacturing tolerances. In this case, the two screws adjust the collimator in horizontal direction, orthogonal to the slits, which is the direction requiring most accuracy. Two screws enable adjusting the front and rear part of the collimator individually. Other directions require less accuracy, but to heavily relieve all requirements of manufacturing tolerance, the most preferred embodiment comprises a total of 5 adjustment screws to also calibrate position along the slit direction, and vertical position and vertical angle.

In one embodiment, the angle of the camshaft (124) is controlled through its cog wheel (1241) which touches an intermediate cog wheel (1231) that is attached to a rotation axis (123) that is hinged between springs (1232A-B). When rotating the intermediate cog wheel axis (123), the cam shaft (124) is rotated. When reaching the angular limit, the cog can flex a little, thanks to its axis being positioned between springs. These springs (1232A-B) relieve tolerance requirements in several other parts, in particular the curved slide (121).

The cog wheel axis is in turn controlled by a lever axis (122), which comprises a cog wheel (1221) and a lever (1223) sliding in a curved slide (121), as the collimator moves vertically. Thus, the embodiment takes advantages of the existing means for vertical movement, rather than introducing another motor or actuator.

In a variation of the embodiment, the curved slide is replaced by a small cam on the scan arm.

Another embodiment may use a dedicated motor (not shown) for selecting collimator. Using special software, the collimator can be activated independently of its vertical position, which may simplify routines for calibration of collimator positions. The motor is attached to the scan arm rather than the collimator, whereby avoiding moving cables or extra weight in the collimator package. Thus, switching active collimator is performed far from the patient breast, whereby avoiding taking space for switching close to the patient.

In a slight variation of the illustrated present invention, the camshaft is replaced by a non-cylindrical shaft. For example, if the contact points are located at opposite sides of the shaft, it is also possible to switch contact points in a shaft with a triangular cross section. It may also be possible to use a cylindrical axis, if it is arranged to move a slightly longer transverse distance towards two sets of contact points in different direction.

Another embodiment does not comprise a cam shaft, and requires no radial play. Instead, the fine adjustment can be achieved by adjusting the frame holding the collimator relative to a cylindrical axis, simply by adjusting eccentricity, i.e. radial offset from an axis. If the mechanical parts are manufactured with good tolerances, it is enough to adjust position across the slits. It is not a problem if the vertical calibration depends on the horizontal calibration, when the calibration tolerance in the vertical direction is coarser than the manufacturing tolerance in horizontal direction. Preferably, there is also a motor in vertical displacement, to correct for a vertical offset but not rotation.

Yet another embodiment uses no rotation at all, and the two collimators are not rigidly attached in an angle. Instead, they are part of a mechanical linkage, wherein the motions follow the paths defined by several links, including relative rotation and translation. Mechanical accuracy is obtained by springs pushing the links to contact points of each collimator. Those contact points may be adjustment screws.

Further embodiments may have 3 collimators, preferably arranged rigidly edge to edge in angles of approximately 120 degrees, in the shape of a half hexagon seen from a frontal view. A more elaborate embodiment may have four collimators, mounted in a shape of rectangular box, further comprising a hinge in each corner, whereby enabling pushing the upper collimator into the box, whereby the lower collimator is exposed to the X-ray source. For safety, more than one collimator cannot be pushed into the box at the same time, thanks to a knob in the rear end of each collimator. A very elaborate apparatus comprises a virtually unlimited number of collimators. The collimators may be attached on a long ribbon with X-ray opaque material in the seams. The selector straightens the ribbon, pulls it and folds it into the radiation shield cover (U.S. Pat. No. 7,440,539).

In one embodiment a spindle device may be used to choose from a large number of collimators. Individual fine adjustment of collimators is achieved by motors controlling the position of the spindle, and individual calibration data is stored in a computer memory. The patient safety is guaranteed by an RFID sensor or electrical switch. Maximum safety is obtained if a part of the collimator acts like a conductor in said switch, connected in serial with a control circuit to the high voltage generator of the X-ray source.

In one embodiment, the vertical motion is tilted, whereby the upper position of the collimator is outside the X-ray field. The collimator selection happens in the upper position, whereby the selected collimator is not within the X-ray path before it has moved down. Embodiments of the present invention can be varied in numerous ways.

Yet another embodiment comprises complete separate mechanics for controlling the collimators individually, including separate means for vertical movements. Each collimator can be moved individually. A control mechanism, e.g. in form of control software is responsible for not lowering both collimators at the same time. For patient's safety, in the upper position, the two collimators are close positioned with a flexible metal shield in between, to never expose a free path from the X-ray source to the patient. As one collimator moves down, it also brings the radiation shield, whose opening is slightly smaller than the collimator.

In one embodiment, the dual collimator is made of at least two sheets, performing a miniature motion relative to each using, e.g. a piezoelectric motor in each corner. For example, the motion may be 150 micrometres. The first sheet comprises two sets of long and narrow slits. The first set of slits corresponds to one collimator position. The second set corresponds to a second collimator position. In each set, each slit corresponds to a line-detector. The second sheet works as a slit selector, which covers either the first or second set of slits in the first sheet. The second sheet has wider slits, in order to relieve tolerances. Otherwise a slight misalignment may cause partial occlusion, and thus causing narrowing of slits in the first sheet.

Thus, in this embodiment the switchable multi-slit collimator may comprise at least two sheets of X-ray opaque material, and a selector for moving the sheets and the sheets comprises X-ray susceptible apertures. The ensemble of the sheets together with the selector generate at least a first and a second pattern of a number of narrow slits. The first pattern essentially matches the second pattern at a cone beam projection, as an implication of both patterns matching the detector.

In a slight variation of this embodiment, some slits from the first and second set are shared, i.e. they coincide in the first sheet. Allowing shared slit offers more freedom in design, as it decreases the prohibited combinations of collimator heights. For shared slits, the second sheet is made to limit extension of the slits in longitudinal direction. Typically, each detector line comprises a few dead regions, and the second sheet covers most of the dead regions.

FIGS. 11a and 11b illustrate two slit patterns 1100a for two collimator heights, wherein the larger pattern 1100b in FIG. 11b is made for a collimator position further from the X-ray source. FIGS. 11c-d illustrate two sheets adapted for generating the patterns in FIGS. 11a-11b, when one sheet is put on top of the other. FIG. 11c illustrates the first sheet 1110c, which is obtained as the union of the two patterns when displaced at one relative offset. FIG. 11d illustrates the second sheet 1110d, which is obtained by using a different relative offset. The slits are also widened in the second sheet, whereby lowering requirements on mechanical tolerances. Preferably, one sheet may also shrink slightly relative the other, to allow a pre-determined small gap between the two sheets. In this version of the embodiment, the first sheet defines the width of the apertures, and the second sheet is essentially a selector sheet for activating apertures or parts thereof. (The slit length is less critical than the slit width, as the detector determines resolution along the apertures.) For readability in FIGS. 11a-11d, this embodiment matches a detector with merely three rows of line detectors, and the slit widths are exaggerated, but this design method is applicable to other numbers of line detectors or slit widths.

Since some slits are shared, all slits have equal width. In other words, the widths do not scale with size of the pattern, resulting in lower X-ray flux for the collimator is far from the X-ray source. Fortunately, it is an advantage rather than a problem, as thin objects tend to require lower flux.

Manufacture of the two sheets may be simplified by attaching each of which to a rigid X-ray susceptible material, before making the slits, which may be annoyingly many and long, and also close to each other.

One embodiment of the present invention is implemented in a Computed Tomography (CT), and the boundary is determined by narrowing the tunnel of the CT.

The mentioned embodiments can be combined, varied and extended by a person skilled in the art.

Figure 12:
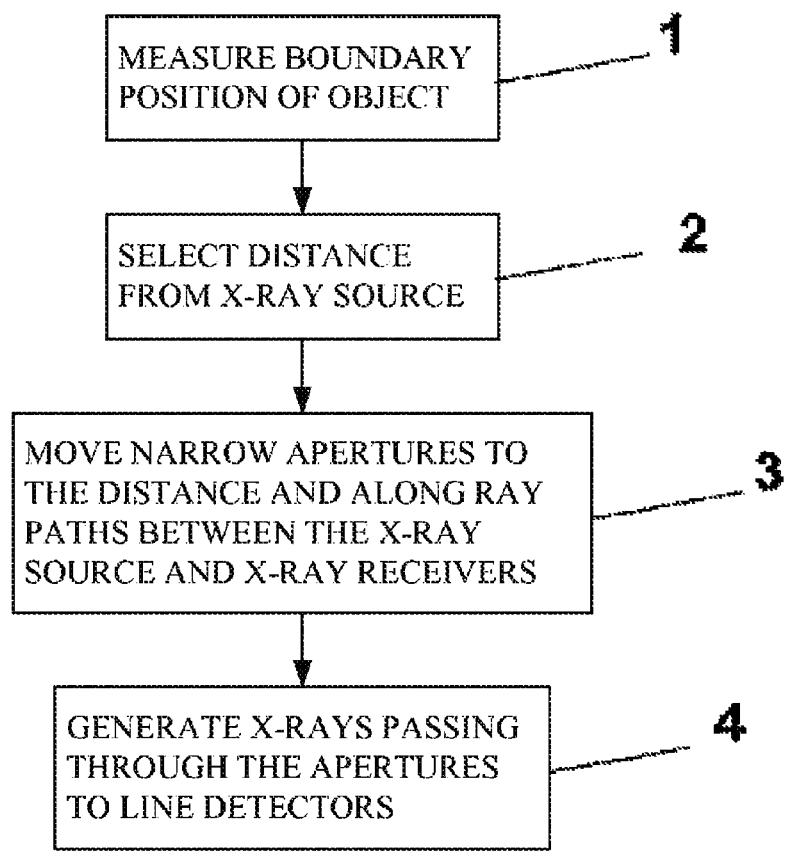
FIG. 12 illustrates a flow diagram illustrating the steps of the present invention.

According to the method of the invention as illustrated in FIG. 12, the method for generating an image of an object in the X-ray apparatus, as described above, comprises the steps of mechanically measuring (1) a boundary position of the object, selecting (2) a distance from the X-ray source, moving (3) several narrow apertures to the distance and along the ray paths between the X-ray source and the X-ray receivers. The selecting of distance is dependent upon the measured boundary position, generation (4) of X-rays passing through the apertures to the line detectors.

The above mentioned and described embodiments are only given as examples and should not be limiting to the present invention. Other solutions, uses, objectives, and functions within the scope of the invention as claimed in the below described patent claims should be apparent for the person skilled in the art.

The invention claimed is:

1. An X-ray apparatus comprising:
    an X-ray source;
    an x-ray detector;
    at least a first collimator having a first active position and a second collimator having a second active position for forming a bundle of X-ray beams, wherein both of said active positions are located in a substantially straight path between said X-ray source and said detector, but at different distances from said X-ray source, wherein said collimators are multi-slit collimators, each of said collimators comprising narrow apertures arranged to match a detector pattern in an active position; and
    a selector arrangement for positioning one of said first or second collimators in said first or second active position, wherein when one of said first or second collimators is in an active position, the other of said first or second collimators is in an inactive position.

2. The X-ray apparatus according to claim 1, further comprising;
    position sensor; and
    a means for selecting one of said collimators, with dependence on a value from said position sensor.

3. The X-ray apparatus according to claim 1, further comprising;
    an X-ray blocking means for blocking a free X-ray path between said collimators, when none of said collimators is arranged to entirely block said X-ray path.

4. The X-ray apparatus according to claim 1, further comprising;
    an X-ray opaque material, arranged between said first and second collimators.

5. The X-ray apparatus according to claim 1, further comprising;
    a common carrying member for holding said first and second collimators rigidly relative to each other, arranged in an angle.

6. The X-ray apparatus according to claim 5, said carrying member is arranged rotatable between a first and a second angle, and said angle is determined by said selector arrangement.

7. The X-ray apparatus according to claim 1, further comprising:
    an arrangement for adjusting said active positions individually or relative to each other.

8. The X-ray apparatus according to claim 1, wherein said selector arrangement further comprises an electrically controlled actuator for said positioning.

9. The X-ray apparatus according to claim 1, said apparatus comprises a displacement means for displacing said collimators in a path towards and away from an imaging zone.

10. The X-ray apparatus according to claim 9, further comprising: spring for applying a force towards a cam.

11. The X-ray apparatus according to claim 1, further comprising:
    a rotor;
    a stator; and
    at least one spring, wherein said rotor comprises said first and said second collimators and a shaft, said spring being arranged to hold said shaft tightly towards contact points in said stator, and said contact points being switched depending on an angle of said rotor relative to said stator.

12. The X-ray apparatus according to claim 1, further comprising:
    a user interface, and said selector arrangement is characterized by dependence on a selection in said user interface.

13. The X-ray apparatus according to claim 12, wherein said selection in said user interface relates to one of a operation mode of said apparatus or a type of examination to be performed in said X-ray apparatus.

14. The X-ray apparatus according to claim 1, wherein said selector arrangement is configured to automatically switch between collimators and corresponding active positions.

15. The X-ray apparatus according to claim 1, further comprising
    a boundary sensing means for measurement position related to available space, and said selector arrangement being setup to depend on information from said boundary sensing means.

16. The X-ray apparatus according to claim 15, further comprising:
    means for adjusting the position of one of said collimators relative to the position of another of said collimator, or individually adjusting each collimator's position at least in a direction transverse to a direction of said narrow apertures.

17. The X-ray apparatus according to claim 1, further comprising:
    a common carrying member for carrying said first and second collimators; and
    a means for rotating said carrying member relative to said detector and said X-ray source.

18. The X-ray apparatus according to claim 17, further comprising;
    a displacement means for moving said common carrying member along a path towards and away from an object.

19. The X-ray apparatus according to claim 1, for imaging of a human breast.

20. The X-ray apparatus according to claim 1, further comprising;
    a compression paddle; and
    a position sensor for measuring a position of said compression paddle, said first and second collimators having narrow elongated X-ray susceptible apertures through one or several plates, wherein the relative positions of said first X-ray susceptible apertures are projections of line detectors of said X-ray detector to said plate or plates at a first distance from said X-ray source, and said second X-ray susceptible apertures are projections of said line detectors to said plate or plates at a second distance from said X-ray source.

21. The X-ray apparatus according to claim 20, comprising a means for selecting one of a set of apertures depending on a value from said position sensor, and furthermore said first distance is different from said second distance.

22. An X-ray apparatus, comprising:
    an X-ray source
    several position sensitive narrow X-ray receivers arranged in a detector pattern;
    a scanning means and
    a switchable multi-slit collimator arrangement for forming a bundle of X-ray beams, said multi-slit collimator arrangement being arranged to switch between at least two positions generating at least a first and second pattern of narrow apertures, wherein said first pattern of apertures matches said detector pattern at a first distance from said X-ray source and said second pattern of apertures matches said detector pattern at a second distance from said X-ray source, wherein said first distance is different from said second distance.

23. The X-ray apparatus according to claim 22, wherein said multi-slit collimator arrangement is arranged to switch between at least a first and second pattern of narrow apertures, wherein said first pattern matches said detector pattern at a first distance from said X-ray source and said second pattern matches said detector pattern at a second distance from said X-ray source, wherein said first distance is substantially different from said second distance.

24. The X-ray apparatus according to claim 23, further comprising a position sensor, and an arrangement for switching said pattern of apertures with dependence on said position sensor.

25. The X-ray apparatus according to claim 22, wherein said switchable collimator arrangement comprises a set of layers of X-ray opaque material arranged in individual patterns, a means for relative displacements of said layers, whereby the combination of said layers generate said first and second pattern of apertures.

26. A method, comprising:
positioning, with a selector arrangement, one of a first collimator or a second collimator in a first active position or a second active position, wherein when one of the first or second collimators is in the active position, the other of the first or second collimators is in an inactive position, wherein the first active position and the second active position form a bundle of X-ray beams for an imaging system including an X-ray source and an x-ray detector, wherein both of the active positions are located in a substantially straight path between the X-ray source and the detector, but at different distances from the X-ray source, and wherein the collimators are multi-slit collimators, each of the collimators comprising narrow apertures arranged to match a detector pattern in an active position.

27. An X-ray apparatus comprising:
an X-ray source;
an x-ray detector;
at least a first collimator having a first active position and a second collimator having a second active position for forming a bundle of X-ray beams, wherein both of said active positions are located in a substantially straight path between said X-ray source and said detector, but at different distances from said X-ray source;
a selector arrangement for positioning one of said first or second collimators in said first or second active position, wherein when one of said first or second collimators is in an active position, the other of said first or second collimators is in an inactive position; and
a common carrying member for holding said first and second collimators rigidly relative to each other, arranged in an angle, wherein said carrying member is arranged rotatable between a first and a second angle, and said angle is determined by said selector arrangement.

28. An X-ray apparatus comprising:
an X-ray source;
an x-ray detector;
at least a first collimator having a first active position and a second collimator having a second active position for forming a bundle of X-ray beams, wherein both of said active positions are located in a substantially straight path between said X-ray source and said detector, but at different distances from said X-ray source;
a selector arrangement for positioning one of said first or second collimators in said first or second active position, wherein when one of said first or second collimators is in an active position, the other of said first or second collimators is in an inactive position;
a common carrying member for carrying said first and second collimators; and
a means for rotating said carrying member relative to said detector and said X-ray source.

* * * * *